US006450188B1

United States Patent
Langhart (10) Patent No.: US 6,450,188 B1
(45) Date of Patent: Sep. 17, 2002

(54) MECHANIZED FUMIGATION TENT

(75) Inventor: Chris Langhart, New Hope, PA (US)

(73) Assignee: Western Industries, Inc., Lester, PA (US)

( * ) Notice: Subject to any disclaimer, the term of this patent is extended or adjusted under 35 U.S.C. 154(b) by 32 days.

(21) Appl. No.: 09/752,387

(22) Filed: Dec. 29, 2000

(51) Int. Cl.[7] .............................................. E04H 15/54
(52) U.S. Cl. .................... 135/115; 135/905; 422/294; 422/28; 422/32; 422/292; 43/124; 426/320
(58) Field of Search ................................. 135/115, 905; 422/28, 32, 33, 292, 294, 306; 426/320, 331, 333, 335; 160/19; 43/124–127

(56) References Cited

U.S. PATENT DOCUMENTS

| | | | | |
|---|---|---|---|---|
| 645,890 A | * | 3/1900 | Conrad | 135/905 |
| 4,033,367 A | * | 7/1977 | Johnston | 135/115 |
| 4,229,914 A | * | 10/1980 | Lucas | 135/115 |
| 5,641,463 A | | 6/1997 | Langhart | |
| 5,918,614 A | * | 7/1999 | Lynch | 135/115 |
| 5,964,236 A | * | 10/1999 | Berke | 135/115 |
| 5,974,740 A | * | 11/1999 | Park | 135/115 |

* cited by examiner

Primary Examiner—Lanna Mai
(74) Attorney, Agent, or Firm—Kenneth P. Glynn, Esq.

(57) ABSTRACT

A fumigation tent includes a frame suspended from a structure by support cables, the frame having an underside; a tarp adapted to be mounted to the top side of the frame, the tarp hanging from the frame defining a tent having a top and side curtains having a lower periphery that defines a bottom perimeter; a sealing arrangement for connecting and sealing the top of the tarp to the frame; a first plurality of cables for raising and lowering the side curtains and being connected to the side curtains and to means for raising and lowering the first plurality of cables; a second plurality of cables for raising and lowering the frame and being connected to the frame and to means for raising and lowering the second plurality of cables.

20 Claims, 6 Drawing Sheets

MECHANIZED FUMIGATION TENT

BACKGROUND OF THE INVENTION

1. Field of the Invention

The present invention relates to a mechanized tent. In particular, it relates to a mechanized tent having a frame and a collectable tarp attached to the frame which can be raised and lowered over pallets of produce or the like, particularly useful for fumigation of produce, e.g. imported products.

2. Information Disclosure Statement

Once fumigated, produce has a shelf life of at most ten days to two weeks. It is therefore desirable to fumigate the produce close to the place where it will be ultimately sold. For imported produce, this place is typically inside a dock building or warehouse located at a port of entry. Pallets of the produce are unloaded from a ship and placed or staged on the floor of the dock building.

Known methods of fumigating produce involve covering the pallets of produce with a polyethylene or plastic impregnated tarpaulin. and then introducing a gas, e.g., methyl bromide, under the tarp to kill live insect infestations. Workers climb on top of the pallets or use poles to pull the tarp over a group of pallets. Because it is necessary for the gas to circulate freely on all sides and the top of the pallets, the tarp cannot lay flat on the top of the pallets. The United States Department of Agriculture requires that a space of about two feet be provided on the top of the pallets, and at least two feet on their sides to allow room for the placement of fans to facilitate the circulation of the fumigation gas. The fans may be tied down with rope to prevent them from moving. Several hoses for introducing the gas is secured to the top of selected fans. The volume of space under the tarp, i.e., the total cubic feet, determines how many fans and point;s of introduction are required.

One method for maintaining the required space on the top of the pallets is to erect wood frames in the shape of a "T" or an "A" at each corner and attach rope between each "T" or an "A" to create a web of support for the tarp. The side space is maintained by draping the tarp outward as it contacts the floor of the dock building and securing it in that position by placing flexible vinyl tubes (approximately 6" in diameter and 4' long) filled with sand on top of the edge of the tarp. At least 2 feet of excess tarp remains beyond the 'sand tubes'.

The steps involved in pulling the tarp over the pallets, setting up the fans, attaching the introduction hoses to the fans, handling hundreds of tubes of sand, and dismantling and storing all of the above equipment, and repeating the process upon completion, require many labor intensive hours.

Improvements to the conventional method of fumigating produce include permanently suspending the tarpaulin from an. overhead frame and lowering the frame over the pallets as needed. Such a frame may be made from welded trusses to form a disassemblable one piece unit of varying dimensions. The typical frame size may be 50 feet long by 250 feet wide, but may be larger or smaller depending upon the spacing between support columns in the dock building. To the underside of the frame a tarpaulin is attached which has been manufactured with grammets, i.e., tabs and eyelets, specific to the frame it hangs from.

The frame may be raised and lowered by a system of cables and pulleys located above the unit which are attached to exposed barjoists on the underside of the roof of the dock building. The cables are connected to hand-operated or motor-operated winchs mounted on the support columns in the dock building. Workers simultaneously crank the winches to lower or raise the frame to a height above the pallets that allows the required 2 feet of space between the tarp and pallets of produce.

A typical tent may be lifted by twelve or more active pickup points. Between each of these points two counter-weight sandbags are deployed to offset the self-weight of the frame and the polyethylene enclosure. Each truss section of the frame spans approximately fifty feet with two mid-point sandbags. These tend to become hung up from friction and pull at an angle to prevent the sandbag from lowering onto the polyethylene enclosure as it is elevated.

A difficult and time-consuming job associated with operating such a system is gathering up the tarp which overhangs from the sides of the frame before the frame is raised. This is necessary because the typical dock building height of about twenty-two feet is limited to about eighteen feet by overhead piping, electrical conduits, etc. When the support frame is raised to the maximum height permitted by these obstructions the tarp hangs down low enough to catch the tops of forklift trucks as they move the pallets of produce in and out of the tent area.

One known way of gathering up the tarp on the sides is to run horizontal plastic pipes through double-thickness portions of the tent walls which form pockets. These pockets can be located at approximately one-third and two-thirds of the wall height and are tied up to the top framing with rope every ten feet or so. Pulled ropes raise the pockets and thus gather the sides of the tent. This method is also time-consuming, however, because it requires numerous tie-up procedures in order to completely raise the tent, e.g., usually at ten to twenty foot intervals around the tent perimeter.

U.S. Pat. No. 5,641,463 utilizes many of the aforementioned improved technique features and additionally incorporates unique features which are more fully discussed in conjunction with some of the drawings described below.

Notwithstanding the above prior art, there is no teaching which anticipates or renders the present invention obvious. Thus, it is neither taught nor suggested to use a system with a ceiling-mounted suspended frame with a fumigation tarp position atop the support frame in a sealed fashion. Likewise, the prior art is deficient in teachings related to cooperating clews or other present invention features, as more fully developed below.

SUMMARY OF THE INVENTION

It is an object of the present invention to provide a large mechanized fumigation tent which incorporates the height of the supporting frame within the tarp structure to eliminate the extra space otherwise needed when the support structure is stacked above the gathered, stored tarp.

It is another object of the present invention to decrease the total weight needed for an efficiently operated fumigation tent.

It is also an object of the present invention to provide a fumigation tent which does not require permanent water storage tanks, related plumbing or the otherwise necessary space which would be occupied by permanent water storage facilities.

It is yet another object of the present invention to provide a large fumigation tent for fumigating produce, logs, textiles, wood products, and other forms of potentially infested imports which can be quickly, conveniently and freely raised and lowered over pallets of the produce.

It is also an object of the present invention to provide a fumigation tent that does not interfere with the operation of forklift trucks as they move pallets of the produce in and out of a tent area and that does not require extensive tie-up procedures to accomplish this.

Another object of the present invention is to provide a fumigation tent which can be raised from a single remote location so that personnel need not be near the tent area after fumigation is complete since exposure to residual gas, which may not have been evacuated from some pallet areas, is possible and can be harmful.

It is yet another object of the present invention to provide for alternative mechanisms for first lifting side curtains of the tarp and then lifting the entire structure and, conversely, lowering the entire structure and then the side curtains of the tarp.

A further object of the present invention to provide a system which seals the tent to the floor of the dock building and which can be easily raised with tent.

The present invention provides a fumigation tent which includes a frame suspended from a structure by support cables, the frame having an underside; a tarp adapted to be mounted to the top side of the frame, the tarp hanging from the frame defining a tent having a top and side curtains having a lower periphery that defines a bottom perimeter; means for connecting and sealing the top of the tarp to the frame; a first plurality of cables for raising and lowering the side curtains and being connected to the side curtains and to means for raising and lowering the first plurality of cables; a second plurality of cables for raising and lowering the frame and being connected to the frame and to means for raising and lowering the second plurality of cables.

The present invention also provides a system for sealing a bottom perimeter of a lower periphery of side curtains of a tent to a floor, which includes at. least one flexible hose mounted along the bottom perimeter for attachment to an external water supply.

The present invention further provides for attachment of the winch cables to clew plates which in turn are attached to winches by winch chains. There is at least one master clew for harmonizing the movement of the first plurality of cables and at least one curtain clew for harmonizing the movement of the second plurality of cables. Preferably, the winches are motorized and can be operated by remote control. (This provides an important safety advantage, because personnel do not have to be near the tent while it is being raised. Therefore, personnel can avoid being exposed to any lingering fumigation gas which is hazardous.) It is also preferable that hand winches with cables be located near the motorized winches, so that they can be attached to the clew plates to provide emergency back up in case electrical problems occur.

Other advantages and characteristics of the present invention will become apparent in view of the description and accompanying drawings that follow.

DETAILED DESCRIPTION OF THE PRESENT INVENTION

Figure 1:
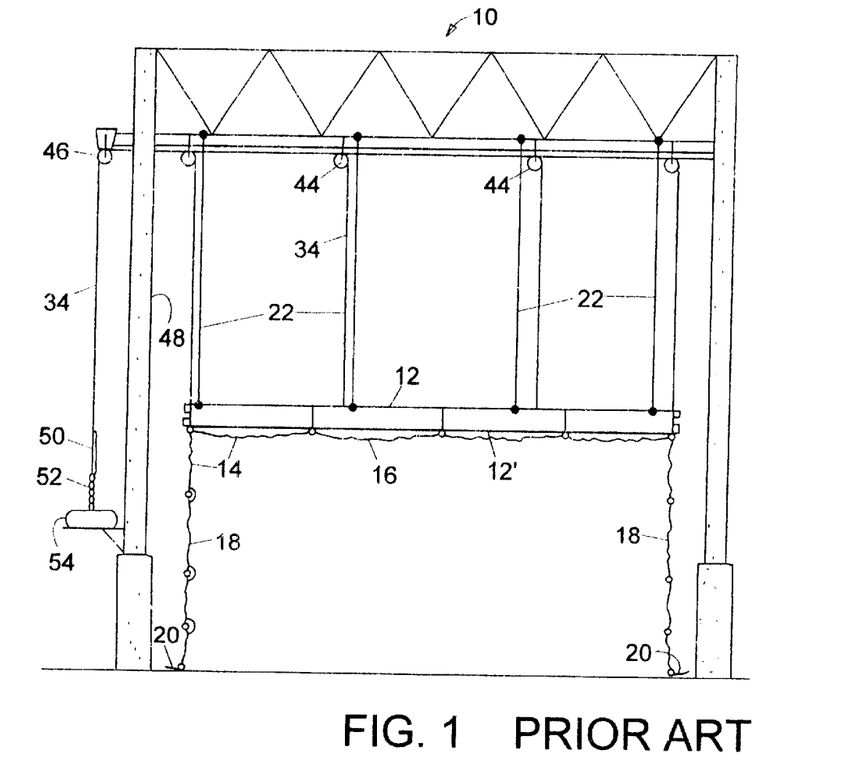
FIG. 1 is a cross-sectional schematic view of a fumigation tent in its lowered position from prior art U.S. Pat. No. 5,641,463.

Referring to the prior art drawings from U.S. Pat. No. 5,641,463 to the present invention herein, shown in the present as FIGS. 1 through 5, the following description is a summary thereof: In FIG. 1, a prior art apparatus for fumigating pallets of produce is indicated generally as apparatus 10. It has a support system for uniformly raising and lowering a tarp enclosure with motorized crank winches while maintaining required clearances, as well as for relocation of frame support cables to vertical positions above the lifting position.

Figure 2:
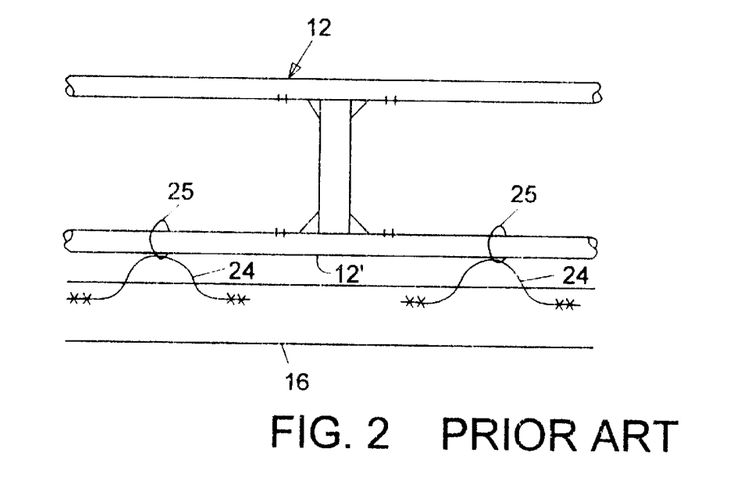
FIG. 2 is a partial side-sectional view of the frame of the tent in FIG. 1 as it is attached to the top portion of the prior art tent.

The apparatus 10 includes a frame 12 and a tarp 14 mounted to the frame underside with tabs 24 and eye rings 25. FIG. 2 shows detail of the top 16 being mounted. The tarp 14 forms a tent with flat top 16, and side curtains 18 having a lower periphery bottom perimeter 20. The frame 12 can be constructed out of aluminum pipes welded and bolted together in a truss-like configuration. However, as will be recognized by those skilled in the art, the frame can be of any shape and construction which is capable of carrying the weight of the tent. The frame 12 may be, for example, suspended from the roof of a dock building or warehouse by support cables 22.

Figure 3:
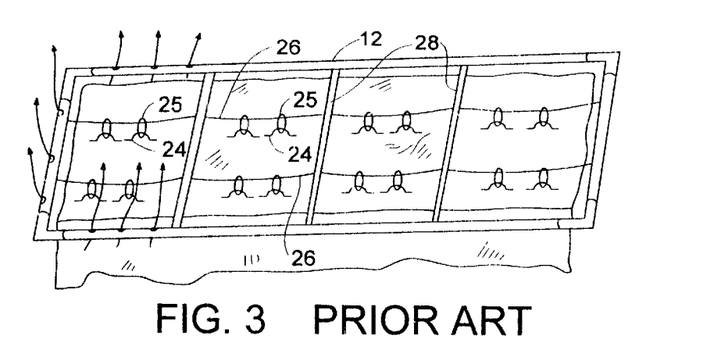
FIG. 3 is a top planar perspective view of the frame and the cables used to support the top middle portion of the prior art tent shown above.

The cables 26 hang between cross bars 28, spaced so that sagging of the top 16 is reduced, usually about every fifteen feet, along cross-sections of the frame 12, as shown in FIG. 3.

Figure 4:
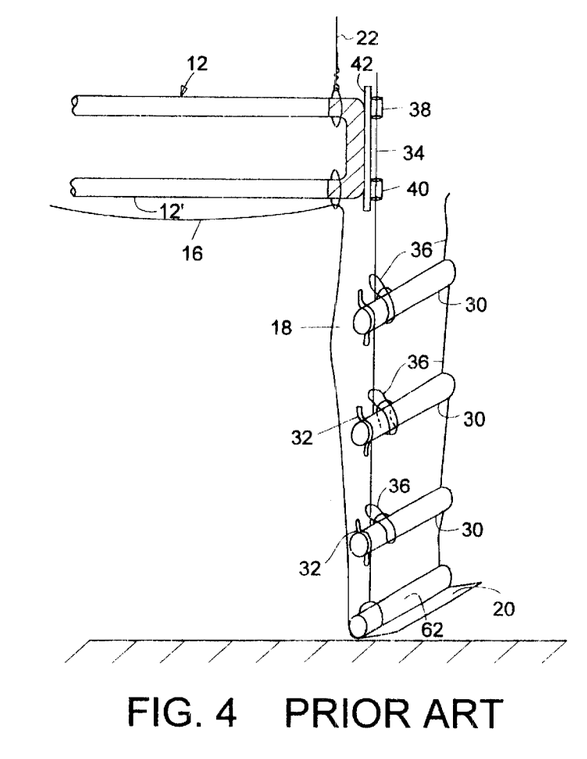
FIG. 4 is a partial perspective view of a side curtain of the prior art tent shown above, with the horizontal bars and rings which are used to support and collect the side curtain while it is being raised.

Horizontal pipes 30 are fitted into tarp pockets 32 formed in double-thickness portions of the side curtains 18, as shown in FIG. 4, located just above the bottom perimeter 20; approximately one-third of the distance between the first interval and the top 16; and approximately two-thirds of the distance between the first interval and the top 16.

Winch cables 34 draw up the horizontal pipes 30. These cables pass through rings 36 attached along and at the ends of the horizontal pipes, as shown in FIG. 4. The tarp pockets 32 are gathered up by the pipes 30, and support the tarp 14 as the horizontal pipes are being raised. Each winch cable 34 passes through a pair of guide tubes 38 and 40 fixed to a plate 42 mounted on the frame 12, also shown in FIG. 4. Guide tubes 38 and 40 and plate 42 provide a means of enabling the frame to be lifted by the winch cables 34 once the horizontal pipes 30 are raised and the tarp is completely collected.

The winch cables 34 pass around roof-mounted pulleys 44 and around pulleys 46 mounted to support columns 48 in the dock building, as shown in FIG. 1. They are attached at their other ends to clew plates 50. Each clew plate 50 can accommodate up to seven or eight winch cables 34, and is attached by a winch chain 52 to a winch 54, as shown in FIG. 1. Winches 54, draw down the clew plates 50 with the winch chains 52, enabling each approximately fifty foot section of the frame 12 to be lifted at twelve or more points. Some of these points are shared with other sections along trusses 28 as required, as shown in FIG. 3.

Figure 5:
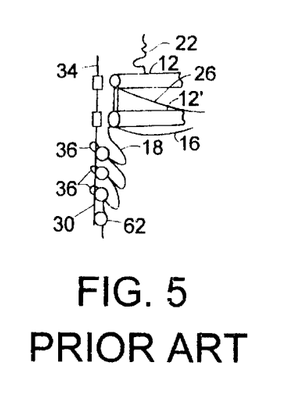
FIG. 5 is a side perspective view of a portion of the above described prior art tent from U.S. Pat. No. 5,641,463 in its raised position.

In the operation of this prior art embodiment, the fumigation tent shown in the aforesaid Figures is raised by reeling in the clew plates 50 with the winches 54, such that the side curtains 18 are drawn upward by winch cables 34 via pulleys 44 and 46. As the winch cables 34 are drawn upward the horizontal pipes 30 on the first interval rise upward. This causes the rings 36 around the winch cables 34 between the first and second intervals of pipes to gather together, thus supporting and collecting intermediate portions of the side curtains 18, and thus preventing the side curtains 18 from "bagging out", i.e., overhanging, to half the height of the side walls of the tent. The rings 36, horizontal pipes 30, and pockets 32 distribute this bagout into several smaller bagouts located between the rings that surround the winch cables 34, so that the overhang created when the tarp 14 is completely gathered up is minimized, as shown in FIG. 5.

Once the first interval of horizontal pipes 30 is drawn up to the height of the second interval, the rings between the second and thirdintervals gather together supporting and collecting the intermediate portions of the side curtains 18. This process continues until all the horizontal pipes 30 and rings 36 are drawn up against the underside 12' of the frame 12. Once the side curtains 18 have been completely raised, and the tarp 14 collected, the winches 54 continue to draw up the winch cables 34, thus raising the frame 12. The winch cables 34 are drawn up until the frame 12 reaches a height which will enable forklift trucks to remove the pallets of produce without interfering with the fumigation tent. From the height where the side curtains 18 are completely gathered up to the height the frame 12 is finally raised to, the support cables 22, deadtied to the roof of the dock building, become limp, i.e., in this interval the frame 12 is supported by the winch cables 34, as shown in FIG. 5.

This prior art fumigation tent is lowered by similar moves for raising the tent described above, except reversing the procedure by reversing the winches, etc. to have the cables, pulleys, etc. operate in the opposite paths as described.

Figure 6:
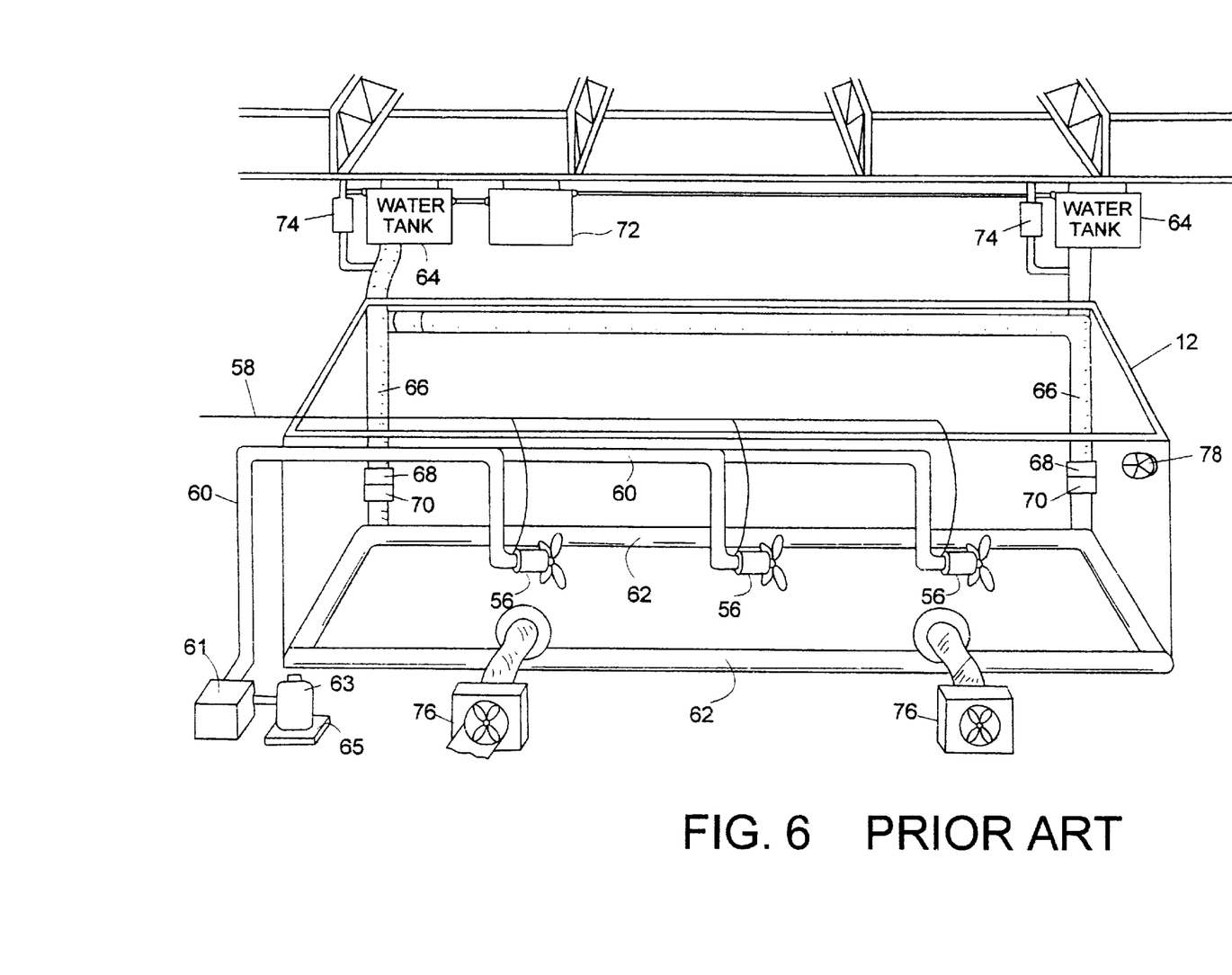
FIG. 6 shows the prior art fumigation tent described above in its lowered positioned, a water supply and removal system, circulation and exhaust fans with their associated wiring, and components of the gas supply system.

Mounting fans 56 and associated wiring 58 on frame 12 is shown in FIG. 6. Entrance hoses 60 for supplying a fumigation gas are positioned near designated fan locations to insure dispersion by mixing concentrated heated gas into the accelerated airstream provided by fans 56. A portion of these hoses rise with the tent, requiring couplings to be made with gas heaters 61 when the tent is lowered. A fumigation gas tank 63, which rests on a beam balance scale 65, supplies the fumigation gas to the heater 61.

Once the tent is in place over the pallets of produce, it must be sealed to the floor of the dock building to create a substantially airtight enclosure, and thus prevent fumigation gas from escaping into the dock building during the fumigation process.

In the disclosed prior art, the method of sealing the tent to the dock floor, is to mount a flexible hose 62 along the bottom perimeter 20 of the tent and fill the hose with water, as shown in FIGS. 4 and 6. The weight of the water secures the tent to the floor of the dock building. The water can be reused by storing it in elevated tanks 64 located above the tent, preferably mounted to the roof of the dock building, as shown in FIG. 6. Collapsible flexible hoses 66 supply water from the elevated storage tanks 64 to the flexible perimeter hose 62. One-way foot valves 68 connected to the collapsible flexible hoses are employed to control columns of water to start the Venturi acceleration process for evacuation of the water from the perimeter hose 62. The foot valves 68 are by-passed by solenoid valves 70 to permit gravity filling of the hose. A compressor 72 supplies air pressure to the tops of the elevated storage tanks 64 to assist in the gravity filling of the flexible perimeter hose 62. Upon returning the water to the tanks, the compressor 72 blows the water from the hose 62 toward the foot valve location where it is carried up by the Venturi.

A water removal system is provided for evacuating the water from the flexible perimeter hose 62 comprising jet pumps 74 located above the tent, preferably mounted to the roof of the dock building, using low-mounted Venturi units which shoot the water up the collapsible flexible hoses 66 into the elevated storage tanks 64. Four distributed storage tanks limit the spilled water to one-quarter of the system's capacity. The compressor 72 can also supply air pressure through the collapsible flexible hoses 66 to assist in evacuating the water from the flexible perimeter hose 62, so that sections of the flexible perimeter hose do not collapse and trap water, thus preventing total water removal.

Once the fumigation process is complete, the fumigation gas is removed by exhaust fans 76 positioned on the floor of the dock building. These fans 76 are used to evacuate the interior of the fumigation tent before the tent is raised. Openings 78 in the tent re-introduce fresh air, as shown in FIG. 6. After approximately two hours of aeration, the tent is raised. It then takes approximately one additional hour for the fumigation gas to disperse to the level where dock personnel can enter the tent area safely.

The foregoing detailed description of the prior art preferred fumigation tent system has many advantages, and the overall concepts therein are incorporated into the present invention. However, numerous disadvantages are also inherent in the above prior art tent systems. These include:

extra space needed overhead to store stacked support frame above the gathered tarp. In some warehouses, dock buildings, etc. there isn't enough clearance to use this prior art system;

costs and space involved in overhead water supply tanks and storage lines;

time and manpower needed to install; operate and maintain overhead water storage;

side curtains taking the weight of the side piping;

side curtains being directly in the chain of upward forces used to lift the main frame, piping and hoses;

inability to support inside fumigation/inspection lines when the support frame is on the outside.

Other disadvantages have been observed.

The present invention, thus, utilizes the conceptual aspects of the prior art system, such as in house ceiling suspension, winch/cable raising and lowering, and water hose bottom periphery sealing. However, in its unique features, the present invention overcomes all of the forgoing prior art shortcomings.

As will be recognized by those skilled in the art, the present invention is not limited to fumigating produce. It can be used to fumigate any article or object that can be placed under the tent. Furthermore, it is contemplated that the present invention can be adapted to be transportable.

Prior art teaches a contiguous impermeable membrane composing the top and sides of the fumigation enclosure hung under the support frame. So as not to be punctured by the support cables, the prior tarp included many support loops allowing the top of the tarp to be supported from the underside of the frame. The prior art top loop supports and the side pipe pockets once employed, approximately double the fabrication cost of the tarp.

Preferred in the present invention, the tarp is attached over the frame. This is an easier installation with the frame resting on the floor than working overhead as before. Further, with the tarp over the support frame, overall thickness of the top of the unit is reduced by almost half because of the inevitable sagging of the tarp top (roof) section is within the height of the support truss in the present invention, rather than below it as in the prior art. In the present invention, the entire system including the tarp are support truss assembly thickness may occupy only about one foot in height.

Previous systems employed custom made flat frames for the perimeter support composed of 2 in. and 2½ in. aluminum pipe. To better resist eccentric forces around the perimeter and perpendicular bending horizontal loads, these frames have been replaced in preferred embodiments with residential commodity antenna truss. The triangle truss sections are about half of the depth of the previous frames, stiffer due to the preferred triangular constriction and about half of cost. Reduced tube diameter and wall thickness of the truss reduce weight over the previous system allowing lifting with fewer winch units.

Figure 7:
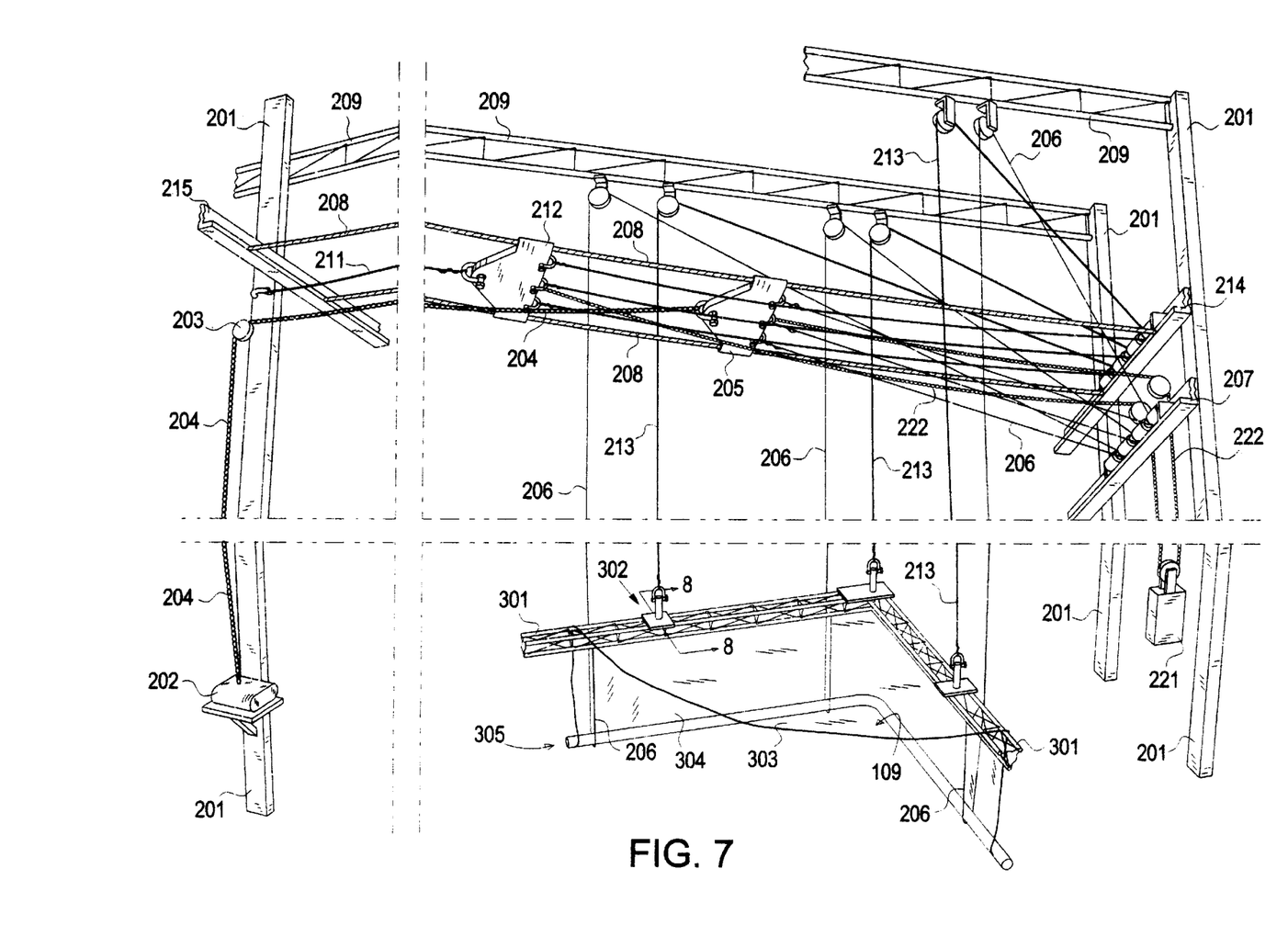
FIG. 7 shows a partial, cut, broken perspective view of one embodiment of the present invention mechanized fumigation tent.

FIG. 7 illustrates one embodiment of the present invention, which system illustrated has several virtues over the previous art. Two of the major advantages are that the system will raise the frame to the ceiling height without disconnecting or replacing with shorter lines, the dead hang low trim frame support cables; a very labor intensive activity. (In the prior art system, raising to and lowering from the ceiling was done periodically to get the prior art frame high enough to accommodate other cargo positioned below, when not in fruit fumigation season). Secondly, the clew system and associated guide and load cables are positioned horizontally eliminating the need for vertical space above the winch equal to or greater than the distance the tent sides must be raised (eliminating the previously required space for the clew to travel).

FIG. 7 illustrates an oblique view of a partial cut representation an architectural situation providing structural support as in a dock building interior. Columns 201 provide support for a winch mounting platform and winch 202. Above are cross-arms with holes 215, 214, 207 permitting attachment of sheaves to permit cords and cables to be variously directed. These cross-arms also support the guide cables that keep the clews from twisting and insure their cooperating operation. Above are roof support bar joists permitting attachment of sheaves, such as sheave 203.

The action of the winch is to first raise the side curtains 304 of the tent up to the level of the support frame. Then further winch operation will raise the entire frame, with side curtains 304 in the raised position, on up toward the underside of the ceiling bar joist's underside. The winch 202 pulls the chain 204 down. This is translated to a horizontal pull by sheave 203. Chain 204 pulls clew 205 which is vertically supported by guide cables 208. The clew allows one cable to pull many cables such as exemplary cable 206 shown in solid lines. The pull on cords 206 is translated into various directions by the sheaves mounted on cross-arm 207. These cords variously arrive at sheaves mounted to the underside of the several roof support bar joists 209. From these sheaves the cords drop down to touch the floor and then return part way up to the support truss frame where they are attached (dead tied). As these cords 206 pass down to the floor they pass under the bottom edge of the tarp 303 toward the inside of the side skirt. The length of the cords 206 as they reach back up to the support truss are adjusted before being dead tied such that the bottom of the side skirt will reach the floor and yet can be gathered tight to the support frame 301 when raised. When so raised, clew 205 pushes into clew 212 as the chain 204 is shortened by the winch pulling. Clew 212 remains 'part way' out on the support cables 208 by reason of the weight of the support frame 301 pulling down on cables 213 (dashed lines). The 'part way' distance is maintained by dead tie cable 211 which is anchored to the left column 201. This distance controls the height that the frame 301 is above the top of the stacks of fruit or other product. The frame is attached to the cable 213 by the FIG. 8 assembly 302 described below in more detail, which allows the tarp 303 to be sealed when over the frame 301 yet permitting the support. When the frame is raised to the ceiling for off season storage, cable 211 goes slack because clew 212 is pushed leftward by clew 205 as the chain 204 is taken up by winch 202. To insure reliable operation, weight box 221 pulls the two clews away from one another to overcome occasional friction of the clews when in close proximity on guide cables 208. Cable 222 connects the two clews and passes around a sheave or sheaves atop the weight box 221. With the sheave support, the vertical travel of the weight is minimized as the clews move.

Figure 8:
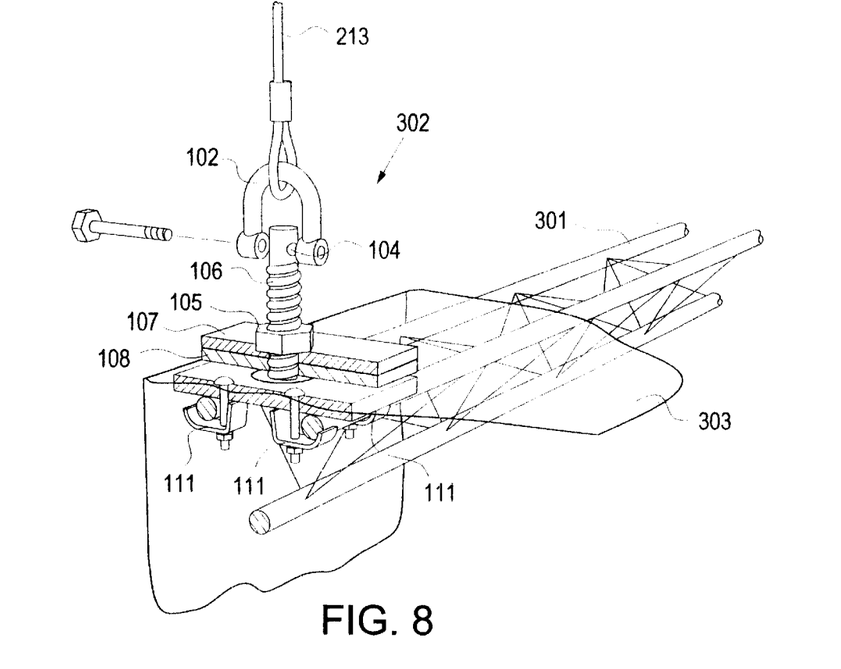
FIG. 8 shows a partial, cut side view of details of the sealing and suspending system for the frame and tarp shown in FIG. 7.

FIG. 8 shows a perspective view of one embodiment of the details of a present invention cable support and seal unit. Support cable 213 is shown and this is the same as cable 213 of FIG. 7. These cables are, for example, spaced approximately at 15 foot intervals around the perimeter. The shackle or quicklink 102 allows fast cable detachment for service. Orifice 104 is for shackle attachment is established on thread rod 106. The lower end of the thread rod 106 is attached to base plate under the tarp 303. Nut 105 compresses stiff plate 107 spreading out the area of force area against closed cell foam 108. The compressed foam area seals the plasticized tarp material against base plate of assembly 302. After the sections of the truss are connected, assemblies such as assembly 302 of FIG. 8, are placed periodically around the perimeter. The tarp 303, fabricated with sides attached, is placed over the truss frame section 301. At the installation location, a small hole is punched in the tarp top to allow passage of the thread rod and eye of assembly 302. A gas tight seal is formed by tightening the nut 105 and compressing the plate 107, foam 108, and the tarp 303 against the base plate of the FIG. 8 assembly 302.

Figure 9:
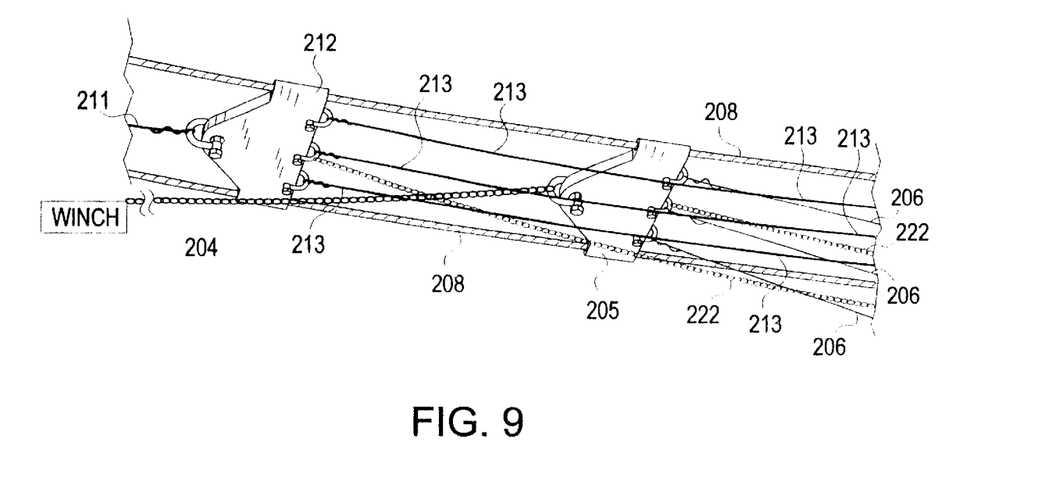
FIG. 9 shows details of the clew arrangement which can be used in the present invention; and, FIG. 10 shows a water delivery system for filling bottom periphery flexible hosing with water for sealing curtain bottom areas.

FIG. 9 illustrates a perspective view of details of a sequential clew arrangement which may function in the same fashion as the clews of FIG. 7. Here, guide wires 208 carry two clews, curtain clew 205 and master clew 212 (referred to as master clew because it is connected to the cables connected to the support frame.)

Curtain clew 205 is connected to curtain cables 206. When curtain clew 205 is pulled to the left by cable 204 and the attached winch, it advances a distance before it contacts and moves clew 212. During this traverse, it raises curtains to a fully pulled up position. When it travels further, it moves along clew 212 to raise up the entire support structure. Clew 212 is connected to support structure (frame) cables 213. When lowering (unwinding) the winch for the clews to move left to right, restraint line 211 stops the lowering of the frame at the desired height above the produce or other items to be fumigated. Counterweights may be included (not shown) to assure the continued movement of the clews, including clew 205 away from clew 212 for complete lowering of the curtains, via counterweight chains 222.

With respect to the present invention, a plurality of clew arrangements would be utilized with coordinated or computer controlled coordination of plural winch operation, or a plurality of sequential clews and a small number of winches could be utilized.

Figure 10:
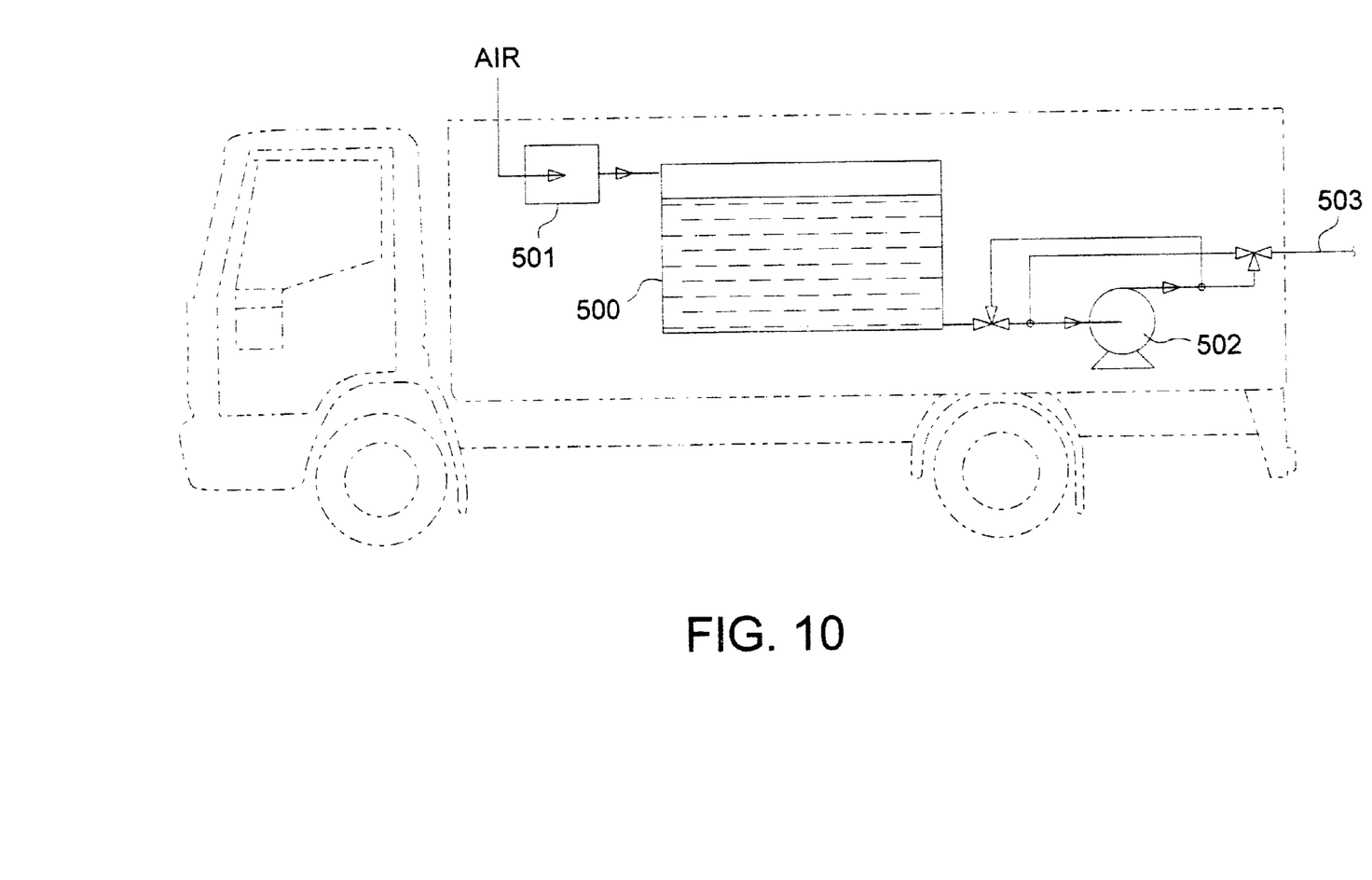

FIG. 10 shows sample external water supply mechanism. Here, it is a portable, mobile system which includes a water tank and pump truck. Often multiple tents are not used simultaneously and the previous system of having tanks and pumping equipment dedicated to each tent has been improved by providing a portable pumping and water supply system usable at various tent locations. This saves costs and installation and maintenance manpower. This portable apparatus functions substantially as the previous system described in prior art except that the water is delivered from a separate, external source and the pump pressures may be reduced as the lift head is less and the foot valves and venturi nozzles would not be required. Initial investment is reduced for each tent as the result of shared facilities. Perimeter hose 305 of FIG. 7, when the tent sides are fully extended downward, rests on the dock building floor. To prevent water ponding, and in the winter icing, the floor of the dock is typically sloped toward the sea, e.g., approximately 18 inches downward for every 100 foot measured perpendicular to the sea-wall. This floor condition requires that water truck connection to be located at the lowest point on the perimeter of the hose 305. Complete drainage pumping and filling are facilitated by working with gravity. Tank 501 has an excess of capacity of the largest perimeter hose volume. A pump 502 with valving for pressure and suction device connects to service hose 503. Air pump 501 hastens water delivery.

The present invention also provides other labor and cost saving aspects compared to the prior art systems. For example:

Gathering of the side curtains by having the cords reach under the bottom perimeter of the tarp sides makes a neater appearance to the folded up tent and takes up much less space. This is partially due to the elimination of the side gathering tubes; (the support rigging and the tubes themselves caused bulk in the folded condition.) Two advantages result here: first is reduced height of the raised total frame and tarp, second is increased ease of installation of the evacuation tubes from fans at the end of the fumigation process. Previously, these had to be installed under the semi-stiff horizontal pipes which made for a less well sealed procedure and also required additional labor to lift side tube weight for insertion of the evacuation hose.

Tarp over frame construction allows the tarp more even support so it can be of thinner material improving packing ability and reducing weight thus requiring fewer winches for a given tent size.

The preferred present invention triangle truss provides a space for supply wiring for the truss mounted circulation fans which may be permanently connected via spring retractable cord winders ceiling mounted above the tent. Also the many sniffer sampling tubes required by the USDA agency can be stored in the truss frame and uncoiled as needed.

Obviously, numerous modifications and variations of the present invention are possible in light of the above teachings. It is therefore understood that within the scope of the appended claims, the invention may be practiced otherwise than as specifically described herein.

What is claimed is:

1. A mechanized fumigation tent for being suspended from an overhead structure, and for being raised and lowered relative to said overhead structure, which comprises:
   (a.) an overhead structure;
   (b.) a support frame having a top;
   (c.) a tarp mounted atop said frame and hanging from said frame to define a top and side curtains, said curtains having a lower periphery which defines a bottom perimeter;
   (d.) a first plurality of cables, being curtain cables, and communicating with said overhead structure and being connected to said side curtains and adapted for raising and lowering said side curtains relative to said support frame;
   (e.) a second plurality of cables, being frame cables, and communicating with said overhead structure and being connected to said frame and adapted to raise and lower said curtains by raising and lowering said first plurality of cables, and so as to raise and lower said frame and tarp by raising and lowering said second set of cables.

2. The mechanized fumigation tent of claim 1 wherein tent further includes:
   (g.) means for sealing said bottom perimeter of said side curtains.

3. The mechanized fumigation tent of claim 2 wherein said means for sealing is a flexible base mounted along said bottom perimeter for viewing, holding and releasing water from an external water supply, whereby when holding water, will seal said tent to a floor.

4. The mechanized fumigation tent of claim 1 wherein said mechanized cable moving means is at least one winch.

5. The mechanized fumigation tent of claim 1 wherein said first plurality of cables and said second plurality of cables are each connected to at least one clew that is connected to said mechanized cable moving means.

6. The mechanized fumigation tent of claim 4 wherein said first plurality of cables and said second plurality of cables are each connected to at least one clew that is connected to at least one winch.

7. The mechanized fumigation tent of claim 1 wherein said second plurality of cables is connected to said support frame by an attachment arrangement which penetrates said tarp top.

8. The mechanized fumigation tent of claim 7 wherein said attachment arrangement includes tarp top sealing means to prevent fumigation gases from exiting said tent.

9. The mechanized fumigation tent of claim 8 wherein said attachment arrangement is a removable attachment arrangement which includes a plate, a threaded rod, a compressed foam, a compression plate and a nut tightened onto said frame and tarp to establish a seal.

10. The mechanized fumigation tent of claim 1 wherein said support structure is formed of a triangular cross-sectional shape.

11. The mechanized fumigation tent of claim 1 wherein said first plurality of cables is connected to a first clew and said second plurality of cables is connected to a second clew, said first clew is connected to said mechanized cable moving means and said first clew is connected to said second clew whereby said first clew may be moved a first distance to raise said side curtains and may also be moved an additional distance to functionally simultaneously move said second clew therewith to effect raising of said support structure and tarp.

12. The mechanized fumigation tent of claim 11 wherein said mechanized cable moving means is at least one winch.

13. The mechanized fumigation tent of claim 11 wherein said first clew and said second clew are mounted on at least two common guidewires attached to said overhead structure and wherein said second clew is positioned between said first clew and said mechanized cable moving means.

14. The mechanized fumigation tent of claim 12 wherein said first clew and said second clew are mounted on at least two common guidewires attached to said overhead structure and wherein said second clew is positioned between said first clew and said mechanized cable moving means.

15. The mechanized fumigation tent of claim 11 wherein said tent further includes:
(g.) means for sealing said bottom perimeter of said side curtains.

16. The mechanized fumigation tent of claim 15 wherein said means for sealing is a flexible hose mounted along said bottom perimeter for viewing, holding and releasing water from an external water supply, whereby when holding water, will seal said tent to a floor.

17. The mechanized fumigation tent of claim 11 wherein said second plurality of cables are connected to said support frame by an attachment arrangement which penetrates said tarp top.

18. The mechanized fumigation tent of claim 17 wherein said attachment arrangement includes tarp top sealing means to prevent fumigation gases from exiting said tent.

19. The mechanized fumigation tent of claim 11 wherein said attachment arrangement is a removable attachment arrangement which includes a plate, a threaded rod, a compressed foam, a compression plate and a nut tightened onto said frame and tarp to establish a seal.

20. The mechanized fumigation tent of claim 11 wherein said support structure is formed of a triangular cross-sectional shape.

* * * * *